(12) United States Patent
Iyer

(10) Patent No.: US 8,059,386 B2
(45) Date of Patent: Nov. 15, 2011

(54) CAPACITIVE ELEMENTS AND FILTERED FEEDTHROUGH ELEMENTS FOR IMPLANTABLE MEDICAL DEVICES

(75) Inventor: Rajesh V. Iyer, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 697 days.

(21) Appl. No.: 12/183,940

(22) Filed: Jul. 31, 2008

(65) Prior Publication Data

US 2009/0079518 A1    Mar. 26, 2009

Related U.S. Application Data

(60) Provisional application No. 60/975,030, filed on Sep. 25, 2007.

(51) Int. Cl.
  *H01G 4/35* (2006.01)
  *H01G 4/236* (2006.01)
(52) U.S. Cl. ......................... 361/302; 361/307
(58) Field of Classification Search ............. 361/302, 361/307, 310
  See application file for complete search history.

(56) References Cited

U.S. PATENT DOCUMENTS

| | | | |
|---|---|---|---|
| 4,424,551 A * | 1/1984 | Stevenson et al. | 361/302 |
| 4,791,391 A * | 12/1988 | Linnell et al. | 333/184 |
| 4,814,938 A * | 3/1989 | Arakawa et al. | 361/302 |
| 4,943,686 A | 7/1990 | Kucharek | |
| 5,333,095 A | 7/1994 | Stevenson | |
| 5,650,759 A | 7/1997 | Hittman | |
| 5,825,608 A | 10/1998 | Duva et al. | |
| 5,867,361 A | 2/1999 | Wolf | |
| 6,008,980 A | 12/1999 | Stevenson et al. | |
| 6,031,710 A | 2/2000 | Wolf et al. | |
| 6,275,369 B1 | 8/2001 | Stevenson | |
| 6,349,025 B1 | 2/2002 | Fraley | |
| 6,566,978 B2 | 5/2003 | Stevenson | |
| 6,660,116 B2 | 12/2003 | Wolf | |
| 6,768,629 B1 | 7/2004 | Allen et al. | |
| 7,035,076 B1 * | 4/2006 | Stevenson | 361/302 |
| 7,199,995 B2 | 4/2007 | Stevenson | |
| 7,281,305 B1 | 10/2007 | Iyer | |
| 7,502,217 B2 * | 3/2009 | Zhao et al. | 361/307 |
| 7,917,218 B2 * | 3/2011 | Iyer et al. | 607/36 |
| 2003/0123215 A1 | 7/2003 | Allen et al. | |
| 2003/0179536 A1 | 9/2003 | Stevenson et al. | |
| 2005/0092507 A1 | 5/2005 | Marshall | |
| 2007/0217121 A1 | 9/2007 | Fu et al. | |
| 2007/0234540 A1 | 10/2007 | Iyer et al. | |
| 2007/0239223 A1 | 10/2007 | Engmark | |
| 2009/0079517 A1 | 3/2009 | Iyer | |
| 2009/0079518 A1 | 3/2009 | Iyer | |
| 2009/0079519 A1 | 3/2009 | Iyer | |

FOREIGN PATENT DOCUMENTS

DE    86 31 853    11/1988

* cited by examiner

*Primary Examiner* — Eric Thomas
*Assistant Examiner* — David M Sinclair

(57) ABSTRACT

A capacitive element for an implantable medical device feedthrough element includes a bore, to receive a feedthrough member, or pin of the filtered feedthrough element, an external surface extending laterally outward from a first opening of the bore, and a recessed area formed in the external surface and extending about an outer perimeter thereof. The recessed area may provide a location on which to apply a conductive material to form a joint that electrically couples the capacitive element to a ferrule of the filtered feedthrough element.

45 Claims, 12 Drawing Sheets

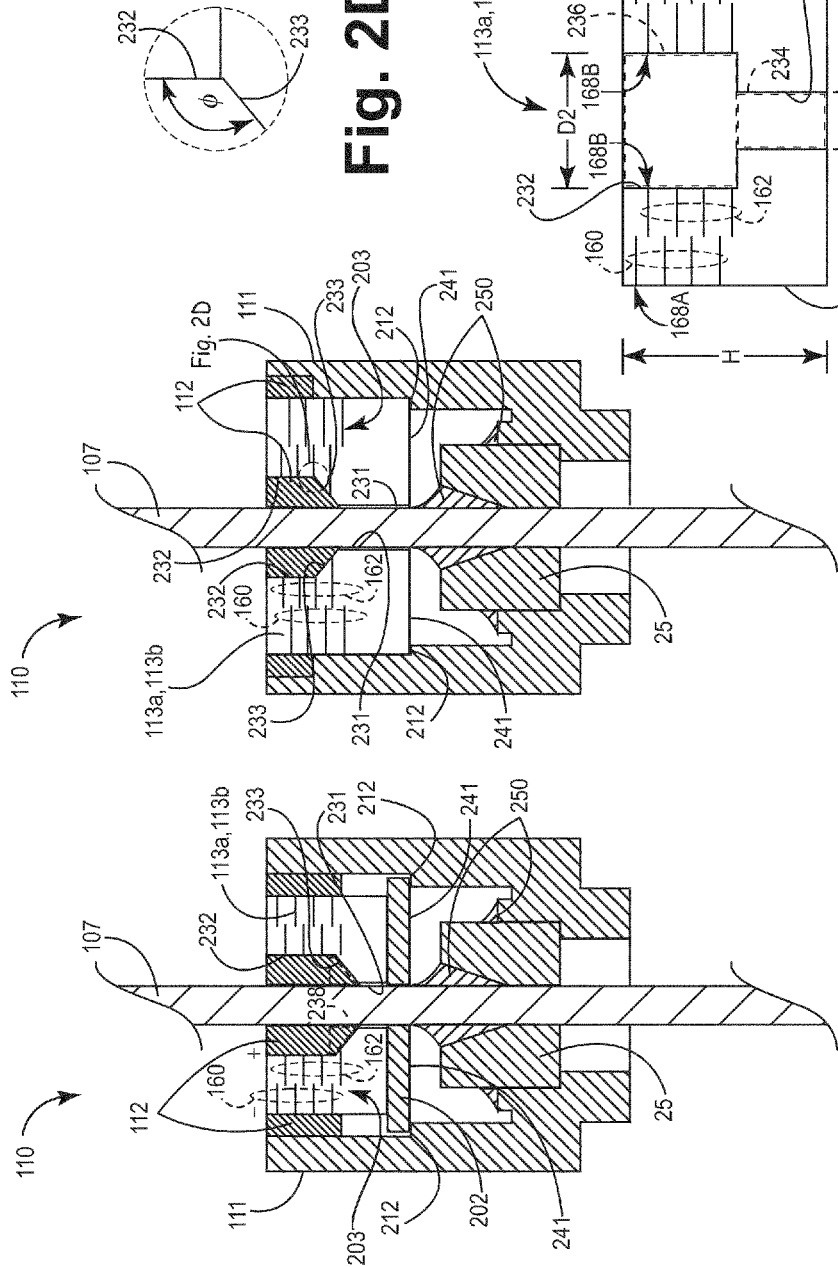

CAPACITIVE ELEMENTS AND FILTERED FEEDTHROUGH ELEMENTS FOR IMPLANTABLE MEDICAL DEVICES

CROSS-REFERENCE TO RELATED APPLICATION

This application claims the benefit of U.S. Provisional Application No. 60/975,030, filed on Sep. 25, 2007, which is hereby incorporated by reference in its entirety.

TECHNICAL FIELD

The present disclosure is directed to implantable medical devices (IMDs), and more particularly, to feedthrough elements for IMDs.

BACKGROUND

Electrical feedthrough elements provide an electrical circuit path extending from the interior of a hermetically sealed housing of an implantable medical device (IMD) to the exterior of the housing. IMDs, such as cardiac pacemakers, implantable cardiovertor defibrillators, neuromuscular stimulators, and physiological monitors, employ such electrical feedthroughs to make electrical connection with leads, electrodes or sensors located outside the IMD housing. A conductive path is provided through the feedthrough by a conductive feedthrough pin which is electrically insulated from the IMD housing. To reduce the effects of stray electromagnetic interference (EMI) signals that may be collected by lead wires electrically coupled to the feedthrough pins, capacitors that perform high frequency filtering, can be included in feedthrough elements.

BRIEF DESCRIPTION OF THE DRAWINGS

The drawings described herein are for illustration purposes only and are not intended to limit the scope of the present disclosure in any way.

FIGS. 2A-2B are longitudinal sectional views of an exemplary feedthrough element through section line A-A of FIGS. 1B-C;

FIG. 2C is a longitudinal sectional view of an exemplary capacitive element;

FIG. 2D is an enlarged view of an angle φ formed by a first and a second surface of a portion of the exemplary capacitive element depicted in FIGS. 2A-2B;

DETAILED DESCRIPTION

Figure 1A:
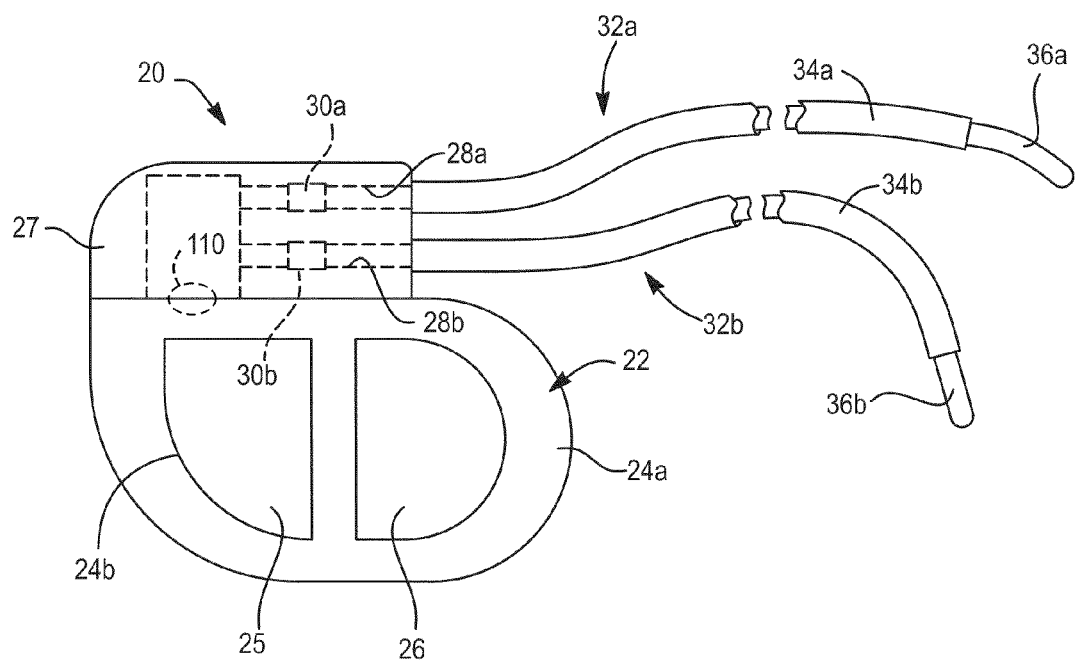
FIG. 1A is a schematic view of an exemplary IMD including a lead connected to a device body.

The following description is merely exemplary in nature and is not intended to limit the present disclosure, application, or uses. The devices described herein include an exemplary number of feedthrough elements etc. Components, including number and kind, may be varied without altering the scope of the disclosure. Devices according to various embodiments may be used in any appropriate diagnostic or treatment procedure, including a cardiac or a neural procedure. For purposes of clarity, similar reference numbers are used in the drawings to identify similar elements.

The present disclosure presents a novel capacitive element that can be employed in a feedthrough element for an implantable medical device. In one embodiment, the capacitive element includes a bore through which the feedthrough member extends. The bore serves to self-align the capacitive element to the feedthrough pin. The capacitive element further includes a first external surface with a recessed area extending about an outer perimeter thereof and being adjacent to the ferrule. Conductive material, disposed over the recessed area, electrically couples the capacitive element to the ferrule.

With reference to FIG. 1A, an implantable medical device (IMD) 20, which can include implantable pacemakers, implantable cardioverter defibrillator (ICD) devices, cardiac resynchronization therapy defibrillator devices, or combinations thereof, is exemplarily illustrated. IMD 20 can include an implantable case, housing or body assembly 22. Implantable case 22 can be formed of appropriate materials and include appropriate features, such as a hermetically sealed body wall 24a. Body wall 24a comprises substantially conductive material such as titanium.

Contained within or associated with case 22 can be a power device 25 such as one or more batteries and/or capacitors encased in housing or case body wall 24b, a controller assembly 26, and a connector body 27. Controller assembly 26 can include a circuit board having a processor, memory, transmitter, receiver, and other appropriate portions. Connector body 27 can extend from or be integrated with case 22. Connector body 27 can include one or more ports 28a,b that interconnects with one or more connector terminals 30a,b of one or more lead assemblies 32a,b. Exemplary connector bodies 27 can include IS-1 connectors, IS-4 connectors or other suitable connectors. Lead assemblies 32a,b generally include respective lead bodies 34a,b each having a respective tip electrode 36a,b. For example, the first lead assembly 32a can include an active tip electrode 36a and the second lead assembly can include a passive tip electrode 36b.

IMD 20 can include one or more hermetically sealed feedthrough elements 110 or feedthrough assemblies. Feedthrough elements 110 electrically couple electronic components located inside a housing or case body wall 24b with electronic components outside of case body wall 24b. Body wall 24b can comprise an inert material such as aluminum. Feedthrough elements 110 can be placed in a variety of locations on IMD 20. For example, feedthrough elements can be coupled to connector body 27, lead assemblies 32a,b, a power source body wall 24b, and/or body wall 24a for IMD 20.

Figure 1C:
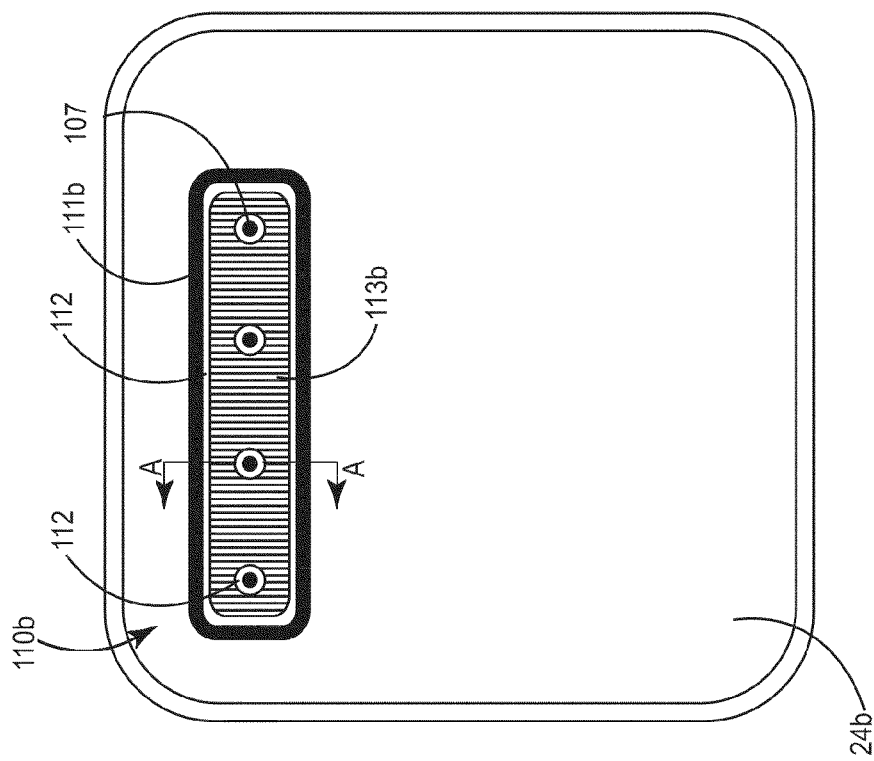
FIG. 1C is a plan view of a portion of the IMD shown in FIG. 1A including a multi-polar filtered feedthrough element.
Figure 1B:
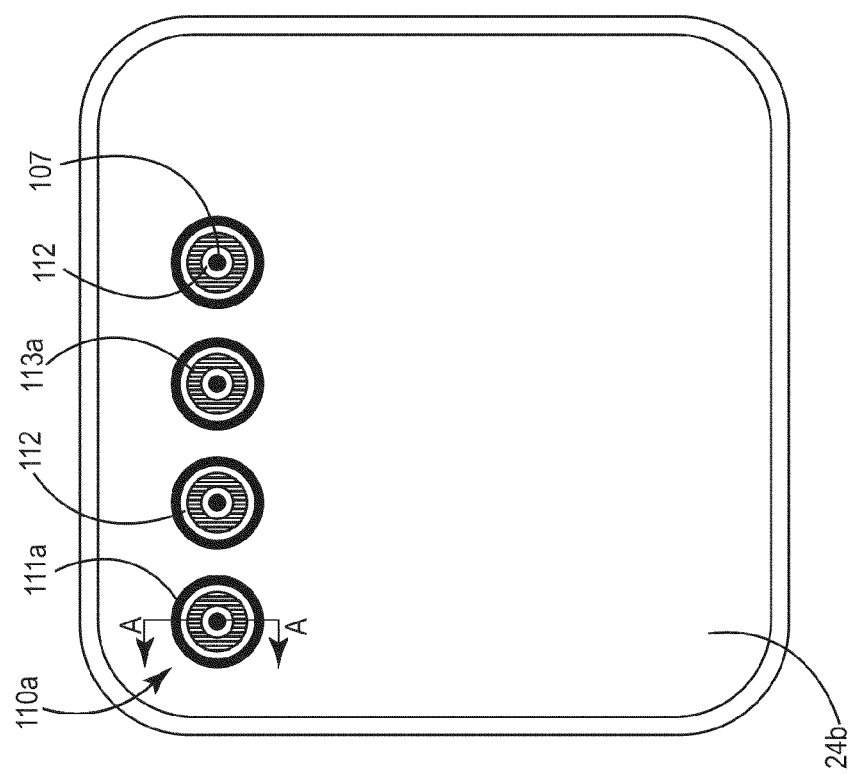
FIG. 1B is a plan view of a portion of the IMD shown in FIG. 1A including a plurality of unipolar filtered feedthrough elements.

A feedthrough element 110 can be a unipolar feedthrough element 110a as generally depicted in FIG. 1B or a feedthrough element 110 can be a multipolar feedthrough element 110b as generally depicted in FIG. 1C. FIG. 1B and, for example, FIG. 2A-2B, and FIGS. 3A-6 can depict a unipolar feedthrough element 110a inserted through an interior side of body wall 24b of a housing for a battery or a capacitor. Each unipolar feedthrough element 110a can include a feedthrough member or pin 107, a ferrule 111a, a capacitive element 113a, an insulator member 25, and conductive material 112 (also referred to as a conductive element). Suitable materials for feedthrough members 107 and ferrule 111a can include titanium, niobium, platinum, platinum/iridium, molybdenum, zirconium, tantalum or alloys thereof. Insulator element 25 can comprise an insulative material such as glass, ceramic or other suitable materials. Conductive material 112 can be a conductive epoxy, a conductive polyimide, a conductive solder or other suitable materials. An exemplary conductive epoxy can be Ablebond 8700E commercially available from Ablestik Inc., located in Rancho Dominguez, Calif.; an exemplary conductive polyimide can include Ablebond 71-1 from Ablestik Inc., and exemplary conductive solders can be iridium-based, tin-based, gold-based solder, and/or silver-palladium.

FIG. 1C and, for example, FIGS. 2A-2B, and FIGS. 3A-7 can depict a multipolar feedthrough element 110b. Feedthrough element 110b is depicted as a quadripolar feedthrough element placed through the interior side of body wall 24b; however, it is appreciated that multipolar feedthrough element 110b can comprise other multiple polar elements. Multipolar feedthrough element 110b can include a single ferrule 121, a single capacitive element 113b, one or more feedthrough members 107, conductive material 112, and an insulator element 25. Single capacitive element 113b can surround more than one feedthrough member 107 such as four feedthrough members 107. Insulator element 25 can include discrete/individual elements, each one surrounding a corresponding feedthrough member 107, or be a single element, surrounding all feedthrough members 107. Feedthrough element 110b can be coupled to a body wall 24b by, for example, welding single ferrule 121 directly to housing body wall 24b.

Insulator element 25 is hermetically sealed within ferrule 111b and around feedthrough member 107 by a joint 250 formed by, for example, brazing, with a suitable material such as gold, titanium, niobium, vanadium, and copper-silver alloys or other suitable material.

Feedthrough member 107 or pin, extends through an aperture located in capacitive element 113a, 113b. Capacitive element 113a, 113b performs high frequency filtering by eliminating signals greater than 450 megaHertz. Capacitive element 113a, 113b can be a discoidal-type capacitor or other suitable capacitor.

As shown in FIGS. 2A-7, capacitive element 113a, 113b can include electrode plates 203 such as a first and a second set of electrode plates 160, 162, respectively. A portion 168A of electrode plates 160 are directly adjacent and exposed at an outer diameter of capacitive element 113a, 113b whereas a portion 168B of electrode plates 162 are placed directly adjacent and exposed at an inner diameter of capacitive element 113a. At least one electrode plate in the first set of electrode plates 160 overlaps, at least slightly, at least one electrode plate in the second set of electrode plates 162. In another embodiment, at least one or more electrode plates in the first set of electrode plates 160 overlaps, at least slightly, at least one electrode plate in the second set of electrode plates 162. Insulative material such as ceramic is disposed substantially around each electrode plate of the first and a second set of electrode plates 160, 162, respectively except a portion 168A, 168B of each electrode plate is exposed at one end of capacitive element 113a, 113b in order to electrically connect with conductive material 112.

The outer surface of capacitive elements 113a,113b, adjacent to the first set of electrode plates 160, and inner surfaces 232 and 233, adjacent to the second set of electrode plates 162, are typically overlaid with a layer of conductive material (not shown), known in the art as termination material, to provide an electrical coupling surface for the electrode plates. Exemplary conductive material includes a silver-palladium such as about 80% by weight of silver and about 20% by weight of palladium. The termination material, in the form of a paste, can be applied, for example, with a paint brush to inner surfaces 232 and 233 so as to prevent the conductive material 112 from extending over first surface 231 (also referred to as a first inner surface). Conductive material 112 is injected from, for example, a syringe into gaps between each ferrule 111a, 111b and corresponding surfaces of capacitive element 113a, 113b.

First set of electrode plates 160 of capacitive element 113a, 113b is electrically and mechanically connected to conductive material 112 disposed adjacent to or over a portion of ferrule 111. Similarly, second set of electrode plates 162 of capacitive element 113a, 113b is electrically connected to feedthrough member 107 through conductive material 112 adjacent to or over feedthrough member 107.

Referring briefly to FIGS. 2A and 2C, capacitive element 113a, 113b can include a first inner surface 231, a second surface 232 (also referred to as second inner surface), and a third surface 233 (also referred to as second inner surface). First inner surface 231 can form a first bore 234, second inner surface 232 can form a second bore 236, and a third inner surface 233 can form a third bore 238. Third inner surface 233 tapers from a diameter of the second bore 236 down to a diameter of the first bore 234. The degree at which third surface 233 tapers depends upon angle φ, as depicted in FIG. 2D. Angle φ is formed by first inner surface 231 and second inner surface 232, which creates a champfer or beveled area. In one embodiment, angle φ can be about 135°. Angle φ can include numerous other embodiments, as indicated in the table below. For example, Table 1 can be read such that angle φ possesses an angle of about 140 degrees. In another embodiment, angle φ can possess an angle that ranges from about 140-150 degrees, and so on.

TABLE 1

| | Angle Φ | |
|---|---|---|
| Embodiment | Angle Φ (degrees) | Range of Angle Φ (degrees) |
| 1 | 90 | 90-100 |
| 2 | 95 | 95-105 |
| 3 | 100 | 100-110 |
| 4 | 105 | 105-115 |
| 5 | 110 | 110-120 |
| 6 | 115 | 115-125 |

TABLE 1-continued

Angle Φ

| Embodiment | Angle Φ (degrees) | Range of Angle Φ (degrees) |
| --- | --- | --- |
| 7 | 120 | 120-130 |
| 8 | 125 | 125-135 |
| 9 | 130 | 130-140 |
| 10 | 135 | 135-145 |
| 11 | 140 | 140-150 |
| 12 | 145 | 145-155 |
| 13 | 150 | 150-160 |
| 14 | 155 | 155-165 |
| 15 | 160 | 160-170 |
| 16 | 165 | 165-175 |

In one embodiment, a maximum gap between first inner surface 231 and a surface of feedthrough member 107 extending therethrough is less than a minimum gap between second inner surface 232 and a surface of feedthrough member 107 extending therethrough. In one embodiment, the minimum gap between second surface 232 and feedthrough member 107, preferably no less than about 0.005 inches, can be filled with conductive material 112. In one embodiment, the maximum gap at first surface 231, preferably no greater than about 0.002 inches, prevents conductive material 112 from flowing below base 202.

In one embodiment, a fit of first internal surface 231 of capacitive elements 113a, 113b about feedthrough member 107, which is preferably a line-to-line fit, effectively isolates, within the ferrule conductive material 112 from brazed joints 250. A line-to-line fit means that the feedthrough member 107 is a close distance between the feedthrough member 107 and first internal surface 231. An external surface 241 of capacitive element 113a, 113b, which extends laterally outward from an opening of the first bore, abuts an internal shelf 212 of ferrule 111a, 111b. An exemplary shelf 212 can possess an outer diameter (OD) that can vary from about 0.003 inches to about 0.025 inches.

Referring to FIG. 2A, a base 202, resting on shelf 212, can be used to support a capacitive element 113a, 113b. Base 202 can be formed by a non-conductive material, for example, polyimide, alumina or other suitable material. An air gap (not shown) exists between shelf 212, capacitive element 113a, 113b and braze joints 250. The air gap is useful for leak testing the seals formed by joints 250 to verify that the seals are hermetic. Although not seen in FIGS. 2A-B, according to some embodiments, a through port (not shown) is located in a sidewall of ferrule 111a, 111b, between shelf 212 and braze joints 250, to allow for the leak testing.

FIG. 2C is a longitudinal sectional view of an alternate embodiment of capacitive elements 113a, 113b, which does not include the third bore 238. FIG. 2C illustrates the second bore, formed by second internal surface 232 and having a diameter D2, in counter-bore relation to the first bore, which is formed by first internal surface 231 and has a diameter D1.

According to some exemplary embodiments of the present disclosure, a diameter of feedthrough member 107 can range between about 0.008 inches and about 0.015 inches, diameter D1 of the first bore 234 can range between about 0.008 inches and about 0.017 inches, and diameter D2 of the second bore 236 can range between about 0.015 inches to about 0.045 inches. A height H 244 of capacitive elements 113a, 113b can be about 0.025 inches for a low voltage feedthrough application, and about 0.075 inches for a high voltage feedthrough application; for the former, a length of the first bore 234 can be about 0.009 inches and, for the latter, about 0.030 inches.

Figure 3A:
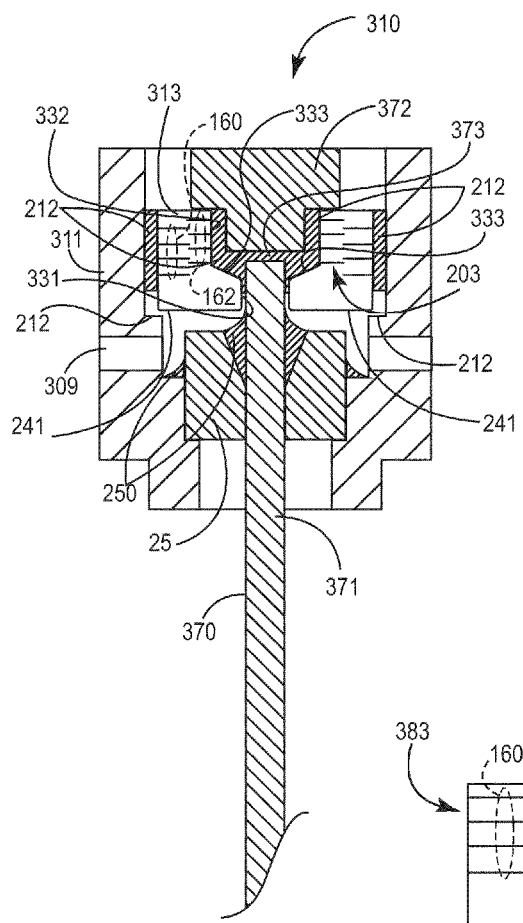
FIG. 3A is a longitudinal sectional view of an exemplary feedthrough element.
Figure 3B:
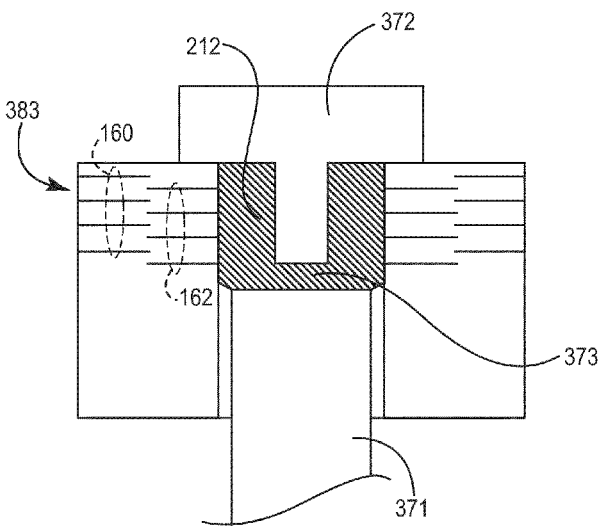
FIG. 3B is a longitudinal sectional view of a portion of another embodiment of a feedthrough element.
Figure 3C:
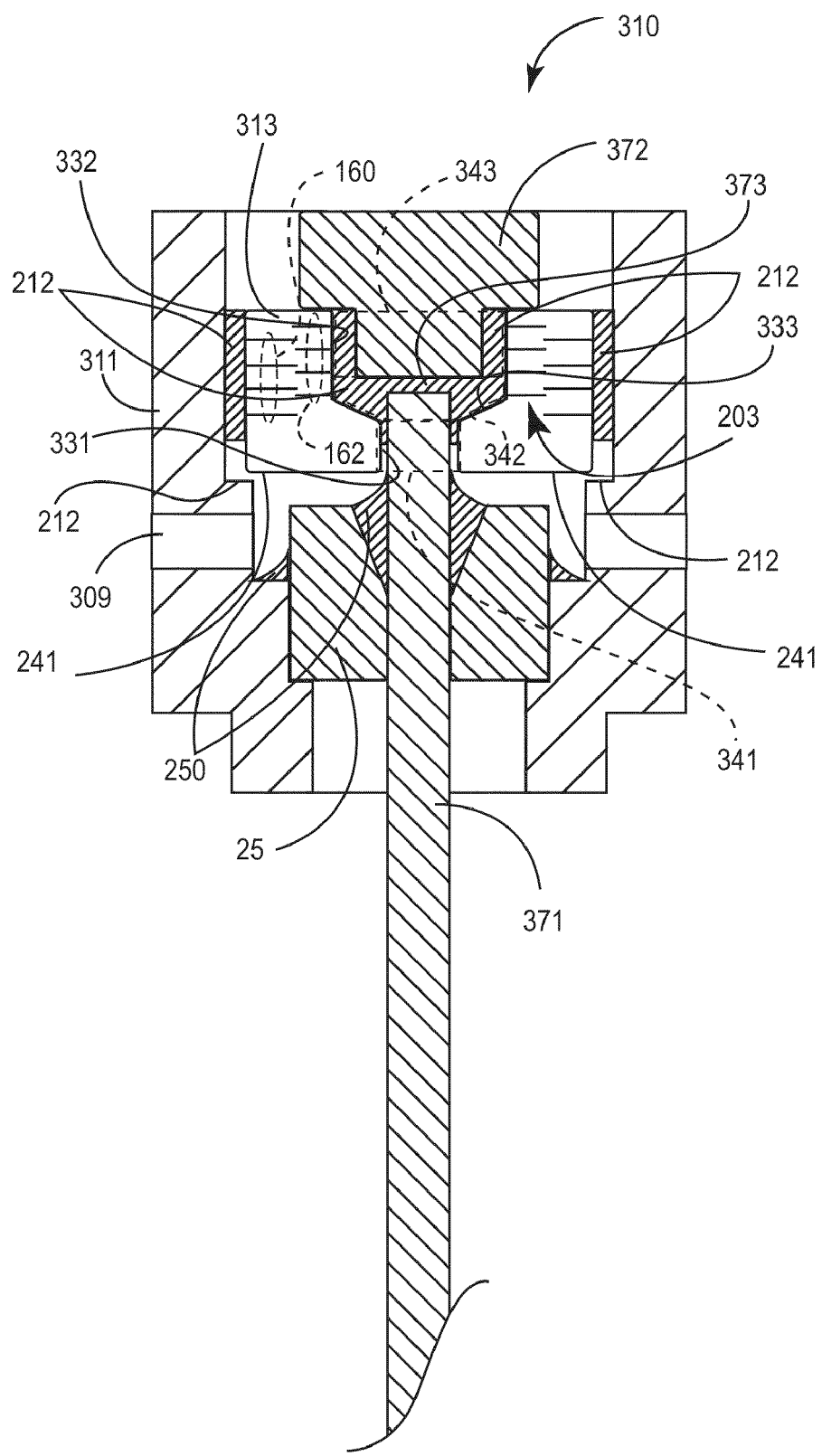
FIG. 3C is a simplified longitudinal sectional view of an exemplary feedthrough element.

FIGS. 2A-B illustrate a first group of embodiments for feedthrough elements 110a, 110b, wherein each feedthrough member 107 is formed by a single pin extending through both the first and second bores 234, 236 of the corresponding capacitive elements 113a, 113b. Turning now to FIG. 3A, feedthrough element 310 is representative of a second group of embodiments. Feedthrough element 310 can be used to bond (e.g. wire bonding, laser bonding etc.) a second portion 372 (also referred to as a nailhead, top-hat, T-shaped pin, or button) to hybrid electronics or a board (e.g. ceramic board, printed circuit board or other substrates). FIG. 3A illustrates feedthrough element 310 that can include a feedthrough member 371 formed by a first portion 370 or pin coupled via a conductive joint 373, to a second portion 372 or pin. First and second portions 370, 372 of feedthrough member 371 can be formed from any of the materials previously described as being suitable for feedthrough member 107. Feedthrough element 310 can be either unipolar, for example, as filtered feedthrough element 110a shown in FIG. 1A, or multipolar, for example, as assembly 110b shown in FIG. 1B, including any number of feedthrough members. FIG. 3A further illustrates a capacitive element 313 of feedthrough element 310 surrounding first and second portions 374 370, 372 and joint 373, within a ferrule 311 of feedthrough element 310. Capacitive element 313 can include a first inner surface 331, which forms a first bore, a second inner surface 332, which forms a second bore, and a third inner surface 333, which forms a third bore and tapers from a diameter of the second bore down to a diameter of the first bore.

Like capacitive elements 113a, 113b, capacitive element 313 can include a plurality of spaced apart electrode plates 203 that comprises a first set of the electrode plates 160 located adjacent an outer surface of element 313, and a second set of the electrode plates 160 that is located adjacent to second inner surface 332. According to the illustrated embodiment, a conductive material 212, forms joint 373 to electrically couple pins 371 and 372 together, and electrically couples the first set of electrode plates 160 to ferrule 311 and the second set of electrode plates 162 to pins 371, 372. Similar to capacitive elements 113a, 113b, an outer surface of capacitive element 313, adjacent the first set of electrode plates 203, and inner surfaces 332 and 333, adjacent the second set of electrode plates 203, are typically overlaid with a layer of conductive material such as the silver-palladium termination material.

In one embodiment, a maximum gap between first inner surface 331 and a surface of pin 371 extending therethrough is less than a minimum gap between second inner surface 332 and a surface of pin 372 extending therethrough. In one embodiment, the minimum gap is large enough to allow filling of conductive material 112 and the maximum gap is small enough to prevent conductive material 112 from flowing past external surface 241 of capacitive element 313. It may be appreciated that, if diameters of pins 371 and 372 are varied with respect to one another, for example as illustrated in the cross-section of FIG. 3B, a capacitive element 383 having a single diameter bore may be employed to achieve the same function as capacitive element 310.

Referring back to FIG. 3A, it may be seen that, like feedthrough elements 110a, 110b, feedthrough element 310 can also include a fit of pin 371 within first internal surface 331 of capacitive element 313, which is preferably a line-to-line fit that effectively isolates within ferrule 311, conductive material 112 from braze joints 250 of insulator element 25. Furthermore, an external surface 341 of capacitive element 313, which extends laterally outward from an opening of the first bore, abuts an internal shelf of ferrule 311, which is formed by a ledge 212 of ferrule 311, so that there is an air gap between capacitive element 313 and braze joints 250 of insulator element 25. FIG. 3A further illustrates ferrule 311 including a through port 309 between ledge 212 and braze joints 250, to allow for leak testing of the seal formed by joints 250 in order to verify that the seal is hermetic.

Figure 4A:
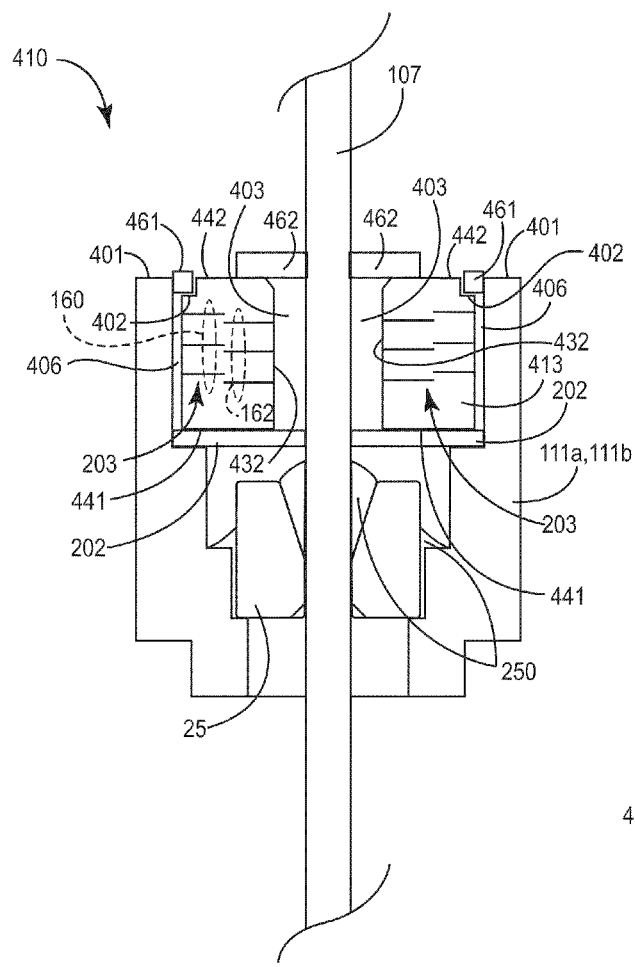
FIG. 4A is a longitudinal sectional view of an exemplary feedthrough element.
Figure 4B:
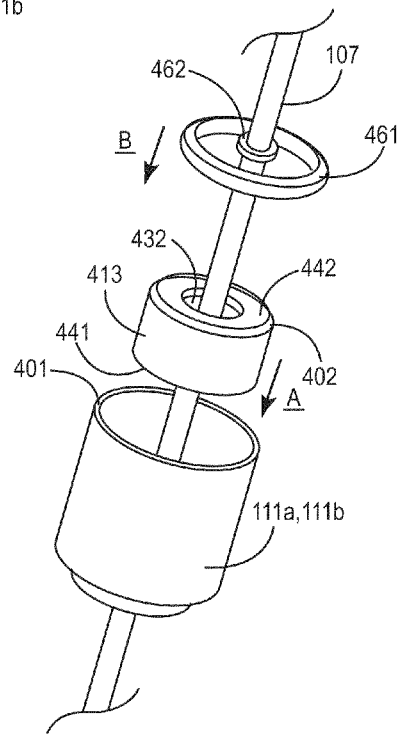
FIG. 4B is an exploded perspective view of the filtered feedthrough element shown in FIG. 4A.

Capacitive elements within feedthrough elements are depicted and described relative to FIGS. 4A-7. FIG. 4A illustrates assembly 410 at an intermediate point within the assembly process. At this stage in the assembly process, braze joints 250 are depicted sealingly engaging insulator element 25 to ferrule 111a, 111b and to feedthrough pin 107 of feedthrough element 410. A capacitive element 413 has been inserted into ferrule 111a, 111b and around feedthrough member 107 such that a first external surface 441 of capacitive element 413 abuts shelf 202 within ferrule 111a, 111b. A first solder preform 461 (preform is also referred to as conductive material, or a conductive element) and a second solder preform 462 are also depicted being mounted on a second external surface 442 of capacitive element 413. First external surface 441 is shown extending laterally outward from a first opening of a bore, which is formed by an internal surface 432 of capacitive element 413, and second external surface 442 is shown extending laterally outward from a second opening of the bore. FIG. 4B, an exploded perspective view of assembly 410, illustrates the insertion of capacitive element 413 into ferrule 111a, 111b, per arrow A, and a mounting of solder preforms 461, 462 onto external surface 441 of capacitive element 413, per arrow B. For the sake of simplicity in illustration, FIG. 4B shows a unipolar embodiment of filtered feedthrough element 410, similar to filtered feedthrough element 110 of FIG. 1A, but filtered feedthrough element 410 can take the form of a multipolar feedthrough element similar to assembly 110b shown in FIG. 1B. Although the embodiments presented herein employ solder preforms, alternate embodiments can employ a solder paste instead of preforms. Preforms 461, 462 can be formed from any suitable solder material known to those skilled in the art, such as tin-based, gold-based, indium-based and any combination thereof.

Exemplary solder material includes tin-based, gold-based, indium-based and any combination thereof. An exemplary alloy used in the solder material can include a range that is about indium (90%)/silver (Ag) 10%). Varying ranges of In/Ag can also be used. In one embodiment, a fluxless and lead (Pb)-free solder can be used to connect one or more feedthrough pins 107 to the capacitive element such as capacitive element 113a, 213, 313, 413. Additionally, fluxless and Pb-free solder can also used to connect the capacitive element 113a, 213, 313, 413 to the ferrule. In another embodiment, potential tensile stresses between the fluxless and Pb-free solder and the capacitor (e.g. inside the capacitor inner diameter (ID), chip capacitor etc.) are substantially eliminated. In one embodiment, "substantially eliminated" means that about 95% of the tensile stresses are eliminated or avoided between the capacitor and the fluxless and Pb free solder. In another embodiment, substantially eliminated can mean that greater than 90% tensile stresses are eliminated. In yet another embodiment, substantially eliminated can mean that greater than 80% tensile stresses are eliminated. Compliant solders can be used to absorb stresses being transferred to the capacitive element. Compliant solders can withstand the rigors of thermal shock tests at a temperatures of about −55° C. to 125° C.), accelerated life tests such as a shock/vibe test, and voltage conditioning tests that can include 168 hours under a bias voltage of about 1000 volts of direct current and 125° C. Exemplary compliant solders can include indium-based alloys such as 90 percent indium and 10 percent silver.

In a subsequent assembly operation, preforms 461, 462 are heated to a temperature in the range of about 150° C. to about 550° C., for example, by placing assembly 410 in a re-flow oven, under vacuum and/or in an inert atmosphere so that the solder material of preform 461 flows into a gap 406, to form a joint that electrically couples the first set of electrode plates 160, which are adjacent an outer surface of capacitive element 413, to an inner surface of ferrule 111a, 111b. The solder material of preform 462 flows into a gap 403 to form a joint that electrically couples the second set of electrode plates 162, which are adjacent inner surface 432 of capacitive element 413, to feedthrough member 107. In one embodiment, a deformation of an edge 401 of ferrule 111a, 111b, caused by temperature associated with the brazing process, for example, greater than 500° C., and/or a tolerance mismatch between ferrule 111a, 111b and capacitive element 413, caused by manufacturing variability, can create some difficulty in assuring that solder preform 461 is properly placed, between ferrule 111a, 111b and capacitive element 413, to flow into, and to bridge gap 406 between element 413 and ferrule 111a, 11b, in order to form an effective electrical coupling therebetween. However, according to the illustrated embodiment, external surface 442 of capacitive element 413 can include a recessed area 402, which is defined by a step that extends about an outer perimeter of external surface 442, adjacent to ferrule 111a, 111b. Recessed area 402 provides a location on which to mount solder preform 461, and thereby alleviate the aforementioned difficulty. A cross-sectional thickness of solder preform 461, extending over recessed area 402, and a corresponding size of recessed area 402, can be of any suitable dimension proportioned to an overall size of assembly 410 and the corresponding range of widths of gap 406. In accordance with one embodiment, a width of gap 406 can range from about 0.003 inches to about 0.006 inches, and a corresponding cross-sectional thickness of solder preform 461 can range from about 0.005 inches to about 0.007 inches. Alternative configurations for providing similar locations on which to mount solder preform 461 are illustrated by the longitudinal sectional views of feedthrough elements 510 and 610, in FIGS. 5 and 6, respectively.

Figure 5:
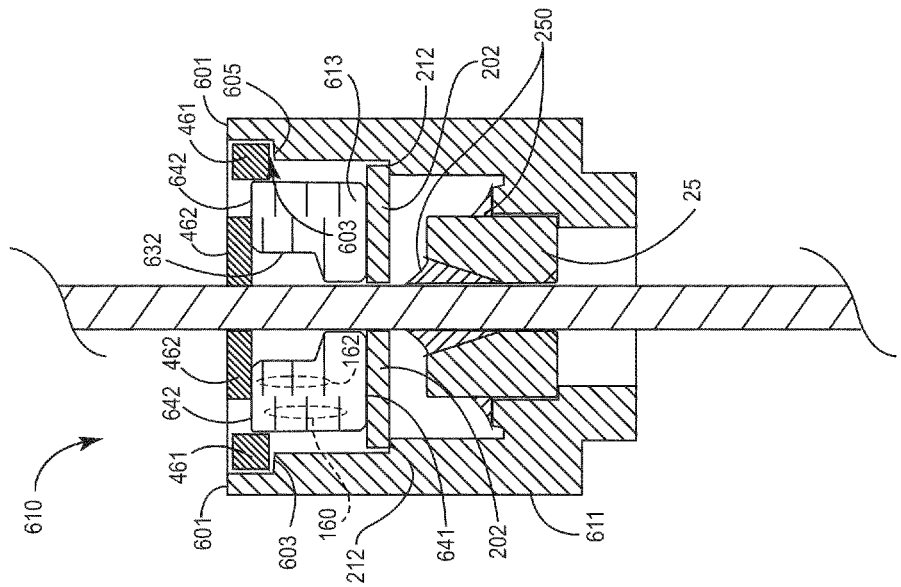
FIGS. 5 and 6 are longitudinal sectional views of exemplary feedthrough elements.
Figure 6:
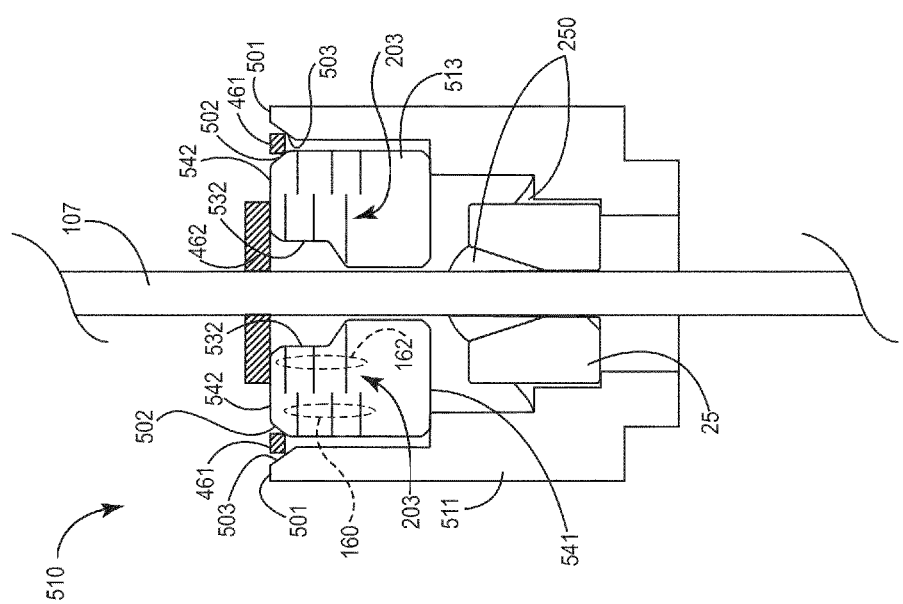

FIG. 5 illustrates a recessed area 502, which is defined by a bevel or chamfer that extends about an outer perimeter of an external surface 541 of a capacitive element 513. Recessed area 502 is shown located adjacent to a recessed area 503 of an edge 501 of a ferrule 511, which recessed area 503 is also defined by a bevel that likewise extends about the outer perimeter of external surface 541. In one embodiment, recessed area 502 of capacitive element 513 in conjunction with recessed area 503 of ferrule 511, form the location on which to mount solder preform 461. FIG. 6 illustrates a recessed area 603 of an edge 601 of a ferrule 611 that is defined by a step 605 extending about an outer perimeter of an external surface 641 of a capacitive element 613. In one embodiment, recessed area 603 forms the location on which to mount solder preform 461. Any suitable combination of the recessed areas shown in FIGS. 4A-6 can be employed by embodiments of the present disclosure.

Figure 7:
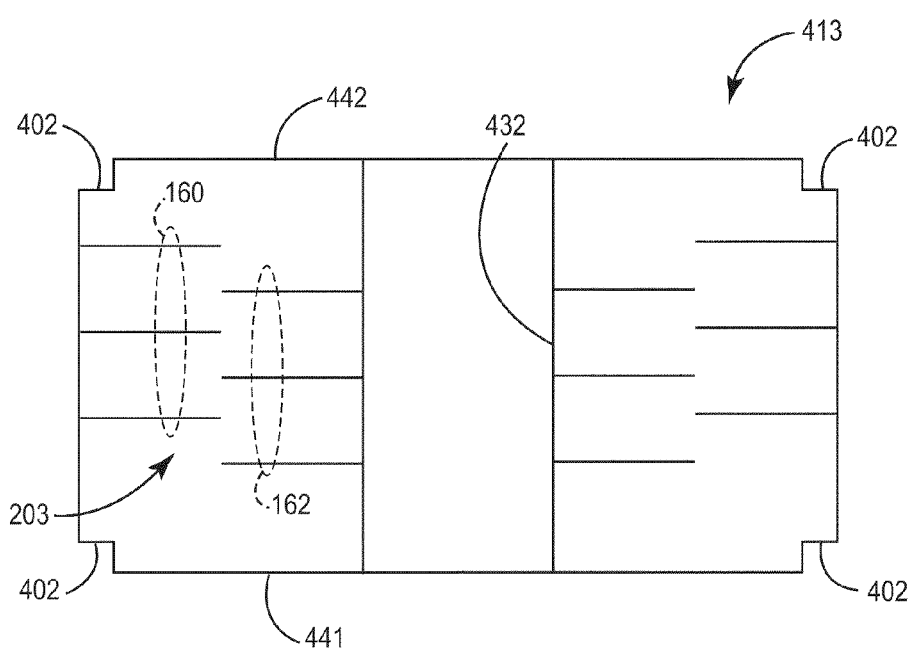
FIG. 7 is a longitudinal sectional view of an exemplary capacitive element.
Figure 8A:
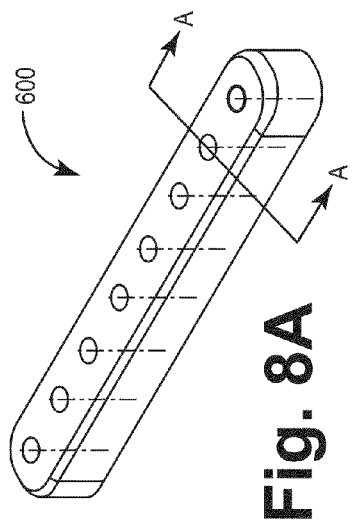
FIG. 8A is a perspective view of an exemplary capacitive element.
Figure 8B:
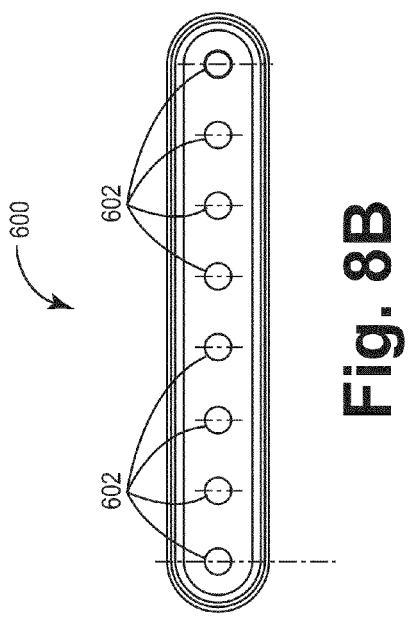
FIG. 8B is a top view of an exemplary capacitive element.
Figure 8D:
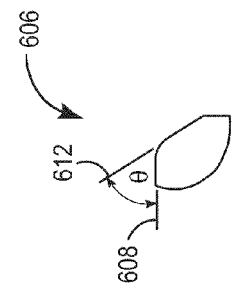
FIG. 8D is an angle of an end of an exemplary capacitive element.
Figure 8C:
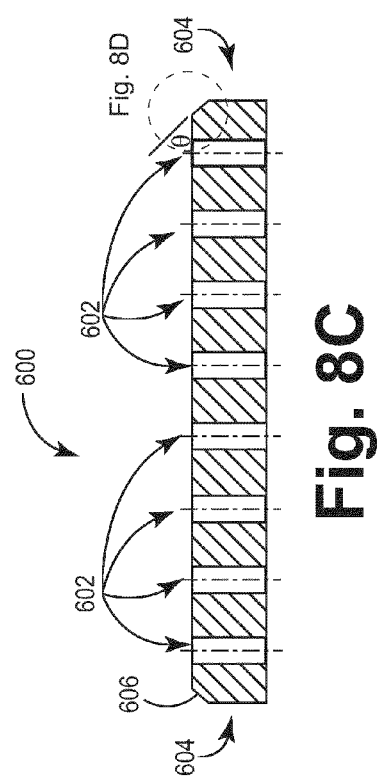
FIG. 8C is a sectional side view of a capacitive element.

Referring back to FIG. 4B, it may be appreciated that capacitive element 413 can be oriented properly for assembly thereof into ferrule 111a, 111b, per arrow A, so that external surface 442 faces away from insulator element 25 and recessed area 402 is adjacent to ferrule edge 401. Turning now to FIG. 7, an alternate embodiment of capacitive element 413 is shown, wherein external surface 441, opposite external surface 442, also includes recessed area 402. In one embodiment, particular attention need not be paid to an orientation of element 413 when assembling element 413 into ferrule 111*a*, 111*b*, per arrow A.

In one embodiment, recessed areas 402, 502, 602 of capacitive elements 413, 513, 613, respectively, are overlaid with at least one layer of a noble metal. Exemplary noble metals include gold, silver, tantalum, platinum, palladium, and rhodium. Preferably gold is used which can be applied via sputtering, for example, DC magnetron sputtering. As solder preform 461 melts, the solder can readily wet to this metalized surface of each recessed area 402, 502, 602. By wetting the metalized surface each recessed area 402, 502, 602, which can enhance a flow of fluxless solder materials.

In one embodiment, metalized surfaces of each recessed area 402, 502, 602 can be formed by sputtering, in series, first titanium (or titanium/tungsten (W)), then nickel (or nickel vanadium), and then gold onto surface 242. In another embodiment, each internal surface 432, 532, 632 of capacitive elements 413, 513, 613, along with each outer surface thereof, are not only overlaid with a layer of the previously described termination material, which is electrically coupled to first and second sets of electrode plates 160, 162, respectively, but are also overlaid with the noble metal layer, which extends over the termination material layer, to enhance the wetting of corresponding melting solder preforms 461, 462 thereto.

Any of the recessed areas, described above, can also be useful in the application of conductive epoxy or conductive polyimide, as an alternative coupling material to solder. A termination material that extends over the outer surface of a capacitive element, for coupling a set of electrode plates of the capacitive element to a ferrule in which the capacitive element is mounted, can further extend into the recessed area of the capacitor, for example, recessed area 402 or 502 of capacitors 413 and 513, respectively. In one embodiment, the bulk of the conductive material 112 can be applied in the recessed area, thereby limiting a flow of the conductive material 112 into the gap between the capacitive element and the ferrule. In another embodiment, any of the other previously described capacitive elements such as capacitive elements 113*a*, 113*b* and 313, along with corresponding filtered feedthrough elements 110*a*, 110*b*, 310 can employ any of the embodiments of recessed areas for mounting a solder preform such as preform 461, or for controlling the flow of conductive epoxy or conductive polyimide.

The present disclosure addresses potential tolerance mismatches between a ferrule and a capacitor by including one or more recessed areas or shelfs on the capacitor outer diameter (OD). The one or more recessed areas helps to bond the solder to the capacitor. Additionally, the close proximity of the preform to the ferrule helps bond the capacitive element to the ferrule as well. Solder can be replaced by conductive epoxy or any other conductive adhesive. The recessed area on the capacitor OD prevents conductive epoxy from flowing into a gap between the capacitor and ferrule, thereby preventing any voltage breakdown below the capacitor. Solder preform has a resting place on the capacitor OD.

Numerous types of capacitive elements can be used to implement the present disclosure. For example, FIGS. 8A-8D depict a capacitive element 600 that includes two or more apertures 602 such as eight apertures in which each aperture 602 surround each pin 107. Capacitive element 600 has an external surface 604 in which at least one or more ends 606 is beveled. End 606 has an angle theta (θ) formed by first and second sides 608, 612. In one embodiment, theta ranges from about 45 degrees to about 70 degrees. In another embodiment, theta can range from about 0° to about 89°. Additionally, Table 2 lists numerous embodiments of theta. For example, Table 2 can be read such that in one embodiment, angle θ can be about 50 degrees. In another embodiment, angle θ can range from about 50 degrees to about 60 degrees, and so on.

TABLE 2

| Embodiment | Angle θ (degrees) | Range of Angle θ (degrees) |
| --- | --- | --- |
| 1 | 15 | 15-25 |
| 2 | 20 | 20-30 |
| 3 | 25 | 25-35 |
| 4 | 30 | 30-40 |
| 5 | 35 | 35-45 |
| 6 | 40 | 40-50 |
| 7 | 45 | 45-55 |
| 8 | 50 | 50-60 |
| 9 | 55 | 55-65 |
| 10 | 65 | 65-75 |
| 11 | 70 | 70-80 |
| 12 | 75 | 75-85 |
| 13 | 80 | 80-88 |

It is appreciated that while theta is depicted with a capacitive element 600 that includes two or more apertures 602, the same principles of a beveled end at an outer diameter applies to a capacitive element with a single aperture therethrough.

Figure 9:
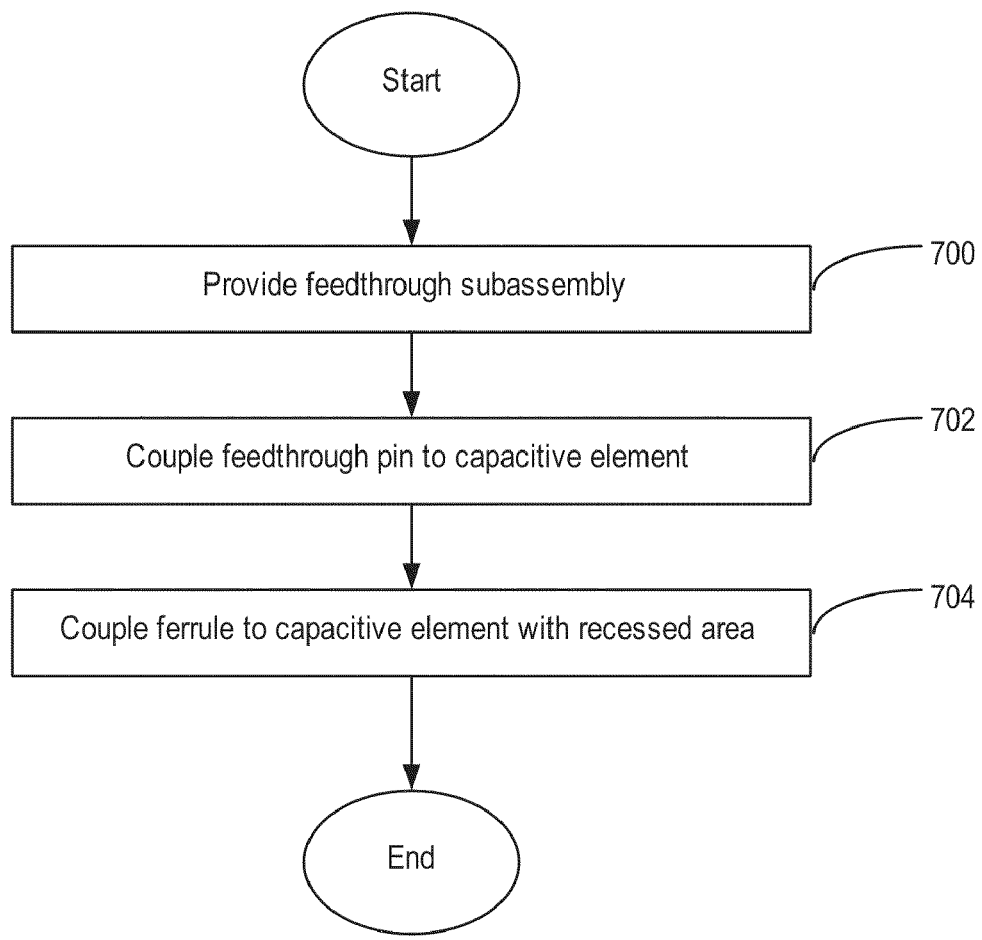
FIG. 9 is a flow diagram for using an exemplary capacitive element.

FIG. 9 depicts a method of using a filtered feedthrough element for an implantable medical device. At operation 700, a feedthrough subassembly is provided. The feedthrough subassembly comprises a ferrule and pin isolated from each other using an insulator that forms a hermetic seal between the pin and the insulator and the insulator and the ferrule. This hermetic seal could be formed using brazing, soldering or glassing. At operation 702, a feedthrough pin extends through a bore of a capacitive element. The capacitive element includes an external surface with at least one recessed area extending about an outer perimeter thereof and being adjacent to the ferrule. At operation 704, the capacitive element is electrically coupled to a ferrule through conductive material over the recessed area.

Figure 10:
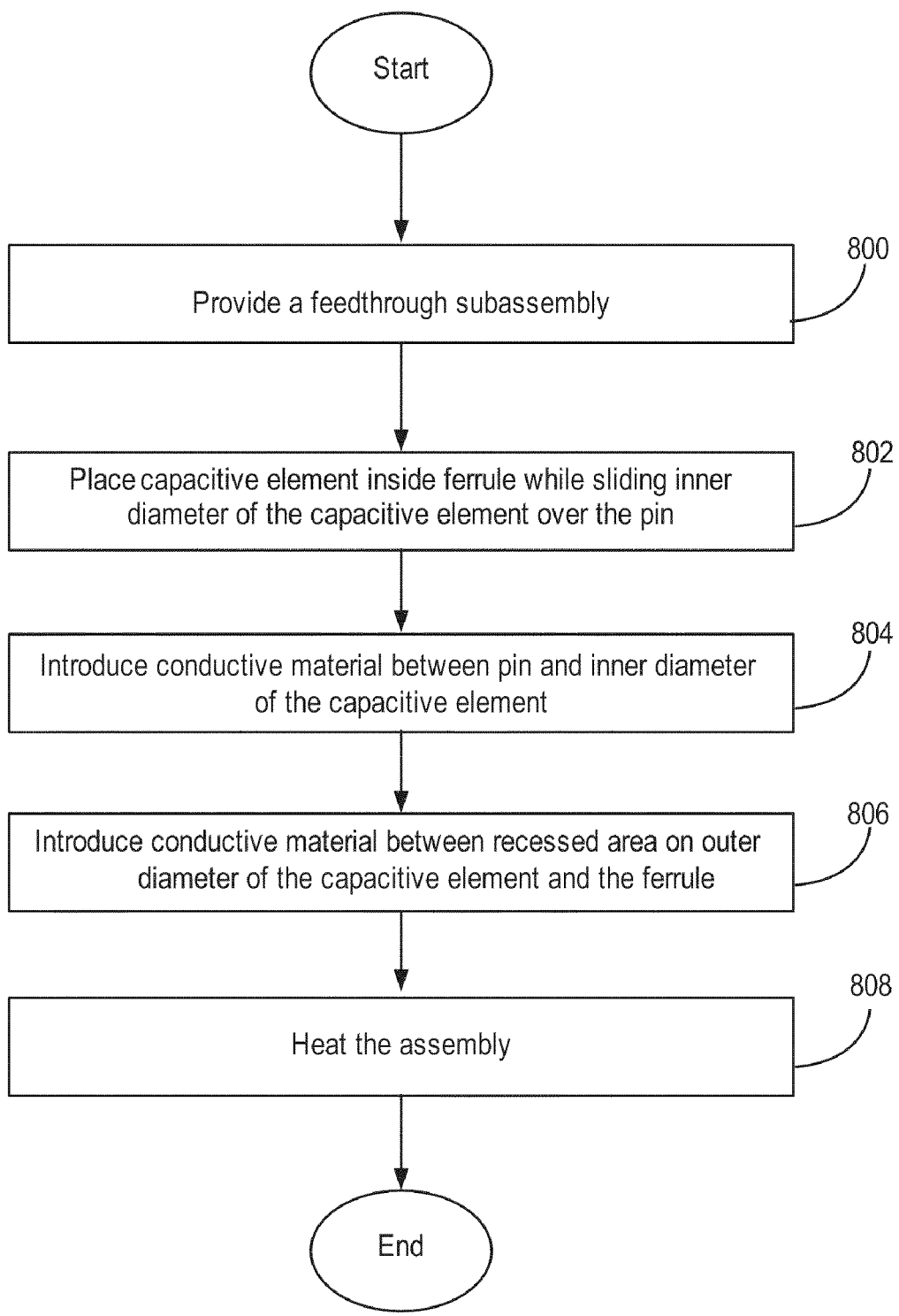
FIG. 10 is a flow diagram for forming an exemplary capacitive element using a conductive epoxy or a conductive polyimide.

FIG. 10 depicts a method of forming a feedthrough element through the use of a conductive material such as conductive epoxy or conductive polyimide. At operation 800, a feedthrough subassembly is provided. The feedthrough subassembly comprises a ferrule and pin isolated from each other using an insulator that form s a hermetic seal between the pin and the insulator, and the insulator and the ferrule. This hermetic seal could be formed using a brazing operation, a soldering operation or a glassing operation. At operation 802, the capacitive element is placed inside the ferrule such that the feedthrough pin is slid through the inner diameter of the capacitive element. At operation 804, conductive material is dispensed or introduced between the pin and the inner diameter of the capacitive element. At operation 806, conductive material is dispensed or introduced between the outer diameter of the capacitive element and the ferrule. The capacitive element includes one or more recessed regions at the outer diameter of the capacitive element. At operation 808, the assembly from operation 806 is placed in a cure oven at 150-250° C. for about 15 minutes to about 2 hours. The cured conductive material thus provides an electrical connection between the capacitive element, the pin and the ferrule of the feedthrough element.

Figure 11:
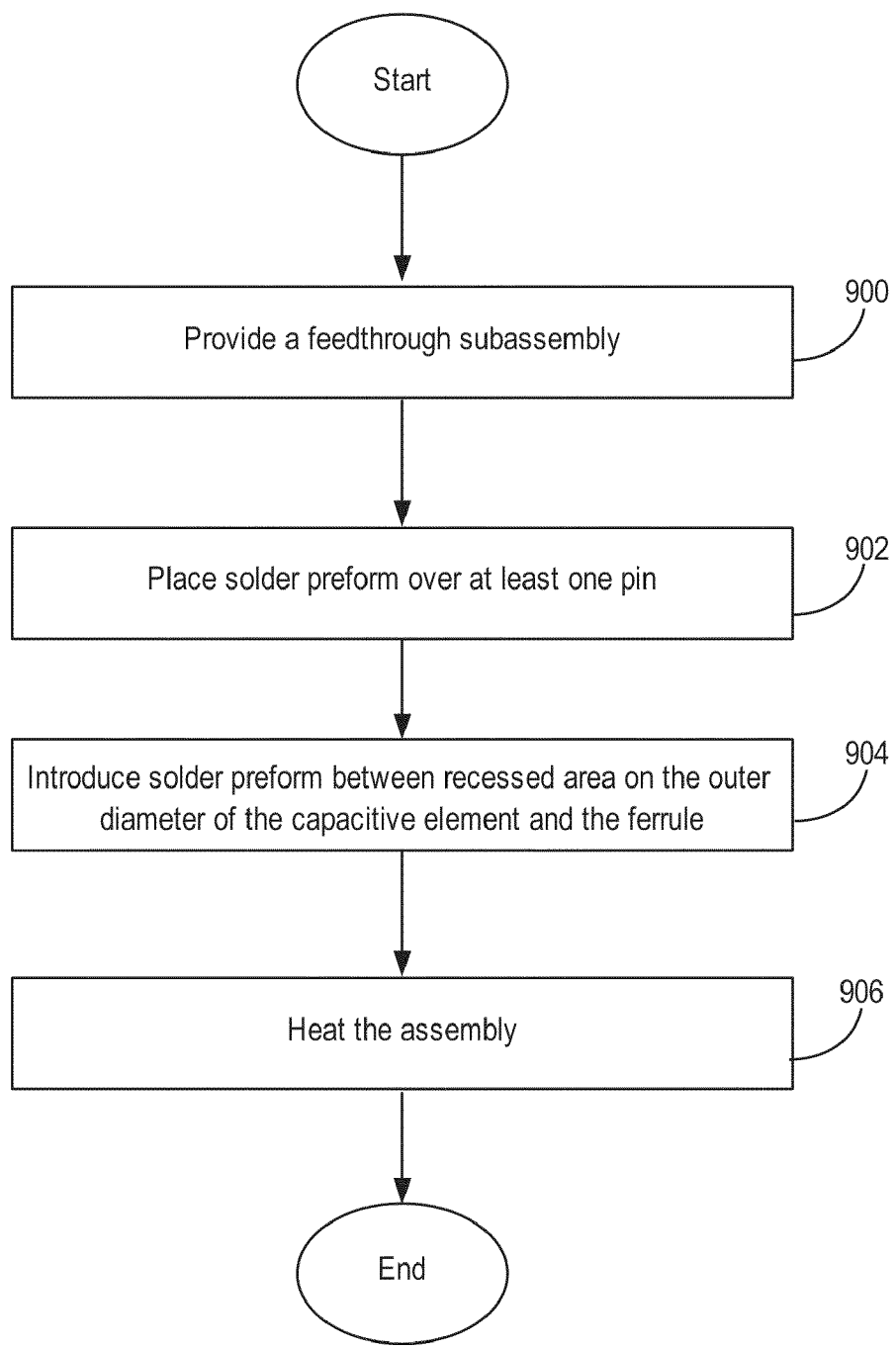
FIG. 11 is a flow diagram for forming an exemplary capacitive element using a solder.

FIG. 11 depicts formation of a feedthrough element through the use solder. At operation 900, a feedthrough subassembly is provided, as previously described. At operation 902, at least one or more solder performs are placed over the feedthrough pin(s). At operation 904, solder performs are placed in the gap between the capacitive element's outer diameter and the ferrule. The capacitive element includes one or more recessed areas at the outer diameter of the capacitive element. At operation 906, heat is applied to the assembly. Specifically, the assembly is placed inside a vacuum reflow oven or an inline oven with an inert atmosphere. Reflow temperatures can range between about 150° C. to about 550° C. Reflowed solder provides an electrical connection between the capacitive element, the pin and the ferrule of the feedthrough element.

While the filtered feedthrough element is depicted as being implemented near the side or body wall of an IMD, filtered feedthrough element can also be used in a connector body such as a IS-4 connector or other types of connector bodies that presently exist. In yet another embodiment, filtered feedthrough element can also be used in a connector body not yet developed. Embodiments of the present disclosure are not limited by any particular number of feedthrough elements or feedthrough members/pins 107. Additionally, while a brazing process is described as being used to form capacitive element, other processes such as a glassing process, which is known in the art.

The present application is related to commonly assigned and co-pending patent application Ser. No. 12/183,953, U.S. Pat. No. 7,928,818, filed on even date herewith, which is hereby incorporated by reference in its entirety.

The present application is related to commonly assigned and co-pending patent application Ser. No. 12/183,922, filed on even date herewith, which is hereby incorporated by reference in its entirety.

In the foregoing detailed description, the invention has been described with reference to specific embodiments. However, it may be appreciated that various modifications and changes can be made without departing from the scope of the invention as set forth in the appended claims.

The invention claimed is:

1. A filtered feedthrough assembly for an implantable medical device, the assembly comprising:
    a ferrule;
    a feedthrough member extending through the ferrule;
    a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, wherein a diameter of the second bore being greater than a diameter of the first bore and the capacitive element further includes a third bore being formed by a surface tapering from the diameter of the second bore to the diameter of the first bore and at least one electrode plate extending away from the second bore and being electrically coupled to the at least one layer of the conductive material; and
    a conductive material extending between the second portion of the feedthrough member and the overlaid surface forming the second bore in order to electrically couple the member to the at least one electrode plate,
    wherein a maximum gap between the first portion of the feedthrough member and the surface forming the first bore being less than a minimum gap between the second portion of the feedthrough member and the overlaid surface forming the second bore.

2. The filtered feedthrough assembly of claim 1, wherein the maximum gap between the first portion of the feedthrough member and the surface forming the first bore being no greater than approximately 0.002 inch.

3. The filtered feedthrough assembly of claim 1, wherein the minimum gap between the second portion of the feedthrough member and the overlaid surface forming the second bore being greater than approximately 0.002 inch.

4. The filtered feedthrough assembly of claim 1, wherein the surface forming the third bore being overlaid with the at least one layer of the conductive material.

5. The filtered feedthrough assembly of claim 1, wherein the at least one layer of the conductive material comprises a first layer directly coupled to the at least one electrode plate and a second layer overlaying the first layer.

6. The filtered feedthrough assembly of claim 1, wherein:
    the ferrule includes an internal shelf; and
    the capacitive element further includes an external surface extending laterally outward from an opening of the first bore, the external surface abutting the internal shelf of the ferrule.

7. The filtered feedthrough assembly of claim 1, further comprising:
    an insulator element located within the ferrule, and surrounding the feedthrough member; and
    an air gap,
    wherein the capacitive element further includes an external surface that extends laterally outward from an opening of the first bore and faces toward the insulator element; and
    the air gap being located between the external surface of the capacitive element and the insulator element.

8. The filtered feedthrough assembly of claim 1, wherein the capacitive element further includes an external surface extending laterally outward from an opening of the second bore, the external surface including a recessed area extending about an outer perimeter thereof and being adjacent to the ferrule.

9. The filtered feedthrough assembly of claim 1, wherein the ferrule includes an edge, and the edge of the ferrule includes a recessed area extending about an inner perimeter thereof, adjacent to the capacitive element.

10. The filtered feedthrough assembly of claim 1, wherein the feedthrough member comprises a single pin extending through the first and second bores of the capacitive element.

11. The filtered feedthrough assembly of claim 1, wherein the feedthrough member comprises a first pin including the first portion of the feedthrough member, a second pin including the second portion of the feedthrough member, and a solder joint coupling the first pin to the second pin.

12. A capacitive element for an implantable medical device feedthrough assembly, the feedthrough assembly including a feedthrough member extending through a ferrule, and the capacitive element comprising:
    a first bore formed, at least in part, by a non-conductive surface and having a diameter;
    a second bore being formed by a surface being overlaid with at least one layer of a conductive material and having a diameter being greater than the diameter of the first bore;
    a third bore being formed by a surface tapering from the diameter of the second bore to the diameter of the first bore;
    and at least one electrode plate extending away from the second bore and being electrically coupled to the at least one layer of conductive material;
    wherein the diameters of the first and second bores are sized to receive the feedthrough member of the feedthrough assembly.

13. The capacitive element of claim 12, wherein the surface forming the third bore being overlaid with the at least one layer of the conductive material.

14. The capacitive element of claim 12, wherein the at least one layer of the conductive material comprises a first layer directly coupled to the at least one electrode plate and a second layer overlaying the first layer.

15. The capacitive element of claim 12, further comprising an external surface extending laterally outward from an opening of the second bore, the external surface including a recessed area extending about an outer perimeter thereof.

16. The capacitive element of claim 15, wherein the recessed area of the external surface being overlaid with a conductive material.

17. An implantable medical device comprising a housing and a filtered feedthrough assembly extending through a sidewall of the housing, the filtered feedthrough assembly comprising:
   a ferrule;
   a feedthrough member extending through the ferrule;
   a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, wherein a diameter of the second bore of the capacitive element being greater than a diameter of the first bore of the capacitive element, and the capacitive element further includes a third bore being formed by a surface tapering from the diameter of the second bore to the diameter of the first bore and at least one electrode plate extending away from the second bore and being electrically coupled to the at least one layer of the conductive material; and
   a conductive material extending between the second portion of the feedthrough member and the overlaid surface forming the second bore in order to electrically couple the member to the at least one electrode plate,
   wherein a maximum gap between the first portion of the feedthrough member and the surface forming the first bore being less than a minimum gap between the second portion of the feedthrough member and the overlaid surface forming the second bore.

18. The device of claim 17, wherein the maximum gap between the first portion of the feedthrough member and the surface forming the first bore of the capacitive element being no greater than approximately 0.002 inch.

19. The device of claim 17, wherein the minimum gap between the second portion of the feedthrough member and the overlaid surface forming the second bore of the capacitive element being greater than approximately 0.002 inch.

20. The device of claim 17, wherein the surface forming the third bore being overlaid with the at least one layer of the conductive material.

21. The device of claim 17, wherein the at least one layer of the conductive material comprises a first layer directly coupled to the at least one electrode plate of the capacitive element, and a second layer overlaying the first layer.

22. The device of claim 17, wherein:
   the ferrule includes an internal shelf; and
   the capacitive element further includes an external surface extending laterally outward from an opening of the first bore, the external surface abutting the internal shelf of the ferrule.

23. The device of claim 17, wherein the feedthrough assembly further comprises:
   an insulator element located within the ferrule, and surrounding the feedthrough member; and
   an air gap,
   wherein the capacitive element further includes an external surface that extends laterally outward from an opening of the first bore and faces toward the insulator element; and
   the air gap being located between an external surface of the capacitive element and the insulator element.

24. The device of claim 17, wherein the capacitive element further includes an external surface extending laterally outward from an opening of the second bore, the external surface including a recessed area extending about an outer perimeter thereof and being adjacent to the ferrule.

25. The device of claim 17, wherein the ferrule includes an edge, and the edge of the ferrule includes a recessed area extending about an inner perimeter thereof, adjacent to the capacitive element.

26. The device of claim 17, wherein the feedthrough member comprises a single pin extending through the first and second bores of the capacitive element.

27. The device of claim 17, wherein the feedthrough member comprises a first pin including the first portion of the feedthrough member, a second pin including the second portion of the feedthrough member, and a solder joint coupling the first pin to the second pin.

28. A filtered feedthrough assembly for an implantable medical device, the assembly comprising:
   a ferrule;
   a feedthrough member extending through the ferrule;
   a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of
   a conductive material wherein the at least one layer of the conductive material comprises a first layer directly coupled to the at least one electrode plate and a second layer overlaying the first layer, and at least one electrode plate extending away from the second bore and being electrically coupled to the at least one layer of the conductive material; and
   a conductive material extending between the second portion of the feedthrough member and the overlaid surface forming the second bore in order to electrically couple the member to the at least one electrode plate,
   wherein a maximum gap between the first portion of the feedthrough member and the surface forming the first bore being less than a minimum gap between the second portion of the feedthrough member and the overlaid surface forming the second bore.

29. The filtered feedthrough assembly of claim 28, wherein the second layer comprises a noble metal.

30. A filtered feedthrough assembly for an implantable medical device, the assembly comprising:
   a ferrule including an internal shelf;
   a feedthrough member extending through the ferrule;
   a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, the capacitive element further includes an external surface extending laterally outward from an opening of the first bore, the external surface abutting the internal shelf of the ferrule; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

31. A filtered feedthrough assembly for an implantable medical device, the assembly comprising:

a ferrule;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, wherein the capacitive element further includes an external surface extending laterally outward from an opening of the second bore, the external surface including a recessed area extending about an outer perimeter thereof and being adjacent to the ferrule; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

32. The filtered feedthrough assembly of claim 31, wherein the recessed area of the external surface of the capacitive element being overlaid with at least one layer of a conductive material.

33. A filtered feedthrough assembly for an implantable medical device, the assembly comprising:

a ferrule including an edge;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, the edge of the ferrule including a recessed area extending about an inner perimeter thereof, adjacent to the capacitive element; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

34. A filtered feedthrough assembly for an implantable medical device, the assembly comprising:

a ferrule;

a feedthrough member extending through the ferrule, wherein the feedthrough member comprises a first pin including the first portion of the feedthrough member, a second pin including the second portion of the feedthrough member, and a solder joint coupling the first pin to the second pin;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

35. A capacitive element for an implantable medical device feedthrough assembly, the feedthrough assembly including a feedthrough member extending through a ferrule, and the capacitive element comprising:

a first bore formed, at least in part, by a non-conductive surface and having a diameter;

a second bore being formed by a surface being overlaid with at least one layer of a conductive material and having a diameter being greater than the diameter of the first bore;

and at least one electrode plate extending away from the second bore and being electrically coupled to the at least one layer of conductive material, wherein the at least one layer of the conductive material comprises a first layer directly coupled to the at least one electrode plate and a second layer overlaying the first layer;

wherein the diameters of the first and second bores are sized to receive the feedthrough member of the feedthrough assembly.

36. The capacitive element of claim 35, wherein the second layer comprises a noble metal.

37. A capacitive element for an implantable medical device feedthrough assembly, the feedthrough assembly including a feedthrough member extending through a ferrule, and the capacitive element comprising:

a first bore formed, at least in part, by a non-conductive surface and having a diameter;

a second bore being formed by a surface being overlaid with at least one layer of a conductive material and having a diameter being greater than the diameter of the first bore;

an external surface extending laterally outward from an opening of the second bore, the external surface including a recessed area extending about an outer perimeter thereof;

and at least one electrode plate extending away from the second bore and being electrically coupled to the at least one layer of conductive material;

wherein the diameters of the first and second bores are sized to receive the feedthrough member of the feedthrough assembly.

38. The capacitive element of claim 37, wherein the recessed area of the external surface being overlaid with a conductive material.

39. An implantable medical device comprising a housing and a filtered feedthrough assembly extending through a sidewall of the housing, the filtered feedthrough assembly comprising:

a ferrule;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, wherein the at least one layer of the conductive material comprises a first layer directly coupled to the at least one electrode plate of the capacitive element, and a second layer overlaying the first layer; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

40. The device of claim 39, wherein the second layer comprises a noble metal.

41. An implantable medical device comprising a housing and a filtered feedthrough assembly extending through a sidewall of the housing, the filtered feedthrough assembly comprising:

a ferrule including an internal shelf;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, the capacitive element further includes an external surface extending laterally outward from an opening of the first bore, the external surface abutting the internal shelf of the ferrule; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

42. An implantable medical device comprising a housing and a filtered feedthrough assembly extending through a sidewall of the housing, the filtered feedthrough assembly comprising:

a ferrule;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, wherein the capacitive element further includes an external surface extending laterally outward from an opening of the second bore, the external surface including a recessed area extending about an outer perimeter thereof and being adjacent to the ferrule; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

43. The device of claim 42, wherein the recessed area of the external surface of the capacitive element being overlaid with at least one layer of a conductive material.

44. An implantable medical device comprising a housing and a filtered feedthrough assembly extending through a sidewall of the housing, the filtered feedthrough assembly comprising:

a ferrule including an edge;

a feedthrough member extending through the ferrule;

a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material, wherein the edge of the ferrule includes a recessed area extending about an inner perimeter thereof, adjacent to the capacitive element; and a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

45. An implantable medical device comprising a housing and a filtered feedthrough assembly extending through a sidewall of the housing, the filtered feedthrough assembly comprising:
- a ferrule;
- a feedthrough member extending through the ferrule, wherein the feedthrough member comprises a first pin including the first portion of the feedthrough member, a second pin including the second portion of the feedthrough member, and a solder joint coupling the first pin to the second pin;
- a capacitive element located within the ferrule and surrounding the feedthrough member, the capacitive element including a first bore being formed by a non-conductive surface extending about a first portion of the member, a second bore being formed by a surface extending about a second portion of the member and being overlaid with at least one layer of a conductive material, and at least one electrode plate extending away from the second bore and being electrically coupled to the at least one layer of the conductive material; and
- a conductive material extending between the second portion of the feedthrough member and the overlaid surface forming the second bore in order to electrically couple the member to the at least one electrode plate, wherein a maximum gap between the first portion of the feedthrough member and the surface forming the first bore being less than a minimum gap between the second portion of the feedthrough member and the overlaid surface forming the second bore.

* * * * *